(12) United States Patent
Kurokawa et al.

(10) Patent No.: US 12,151,030 B2
(45) Date of Patent: Nov. 26, 2024

(54) ADHESIVE PATCH

(71) Applicant: HISAMITSU PHARMACEUTICAL CO., INC., Tosu (JP)

(72) Inventors: Takao Kurokawa, Tsukuba (JP); Hidekazu Kuma, Tsukuba (JP); Masaki Yukuhiro, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 184 days.

(21) Appl. No.: 17/426,796

(22) PCT Filed: Jan. 30, 2020

(86) PCT No.: PCT/JP2020/003491
§ 371 (c)(1),
(2) Date: Jul. 29, 2021

(87) PCT Pub. No.: WO2020/158879
PCT Pub. Date: Aug. 6, 2020

(65) Prior Publication Data
US 2022/0133643 A1 May 5, 2022

(30) Foreign Application Priority Data
Jan. 31, 2019 (JP) .................. 2019-015562

(51) Int. Cl.
| A61K 9/70 | (2006.01) |
| A61K 31/13 | (2006.01) |
| A61K 31/27 | (2006.01) |
| A61K 31/381 | (2006.01) |
| A61K 31/403 | (2006.01) |
| A61K 31/407 | (2006.01) |
| A61K 31/4422 | (2006.01) |
| A61K 31/573 | (2006.01) |

(52) U.S. Cl.
CPC ............ *A61K 9/7053* (2013.01); *A61K 31/13* (2013.01); *A61K 31/27* (2013.01); *A61K 31/381* (2013.01); *A61K 31/403* (2013.01); *A61K 31/407* (2013.01); *A61K 31/4422* (2013.01); *A61K 31/573* (2013.01)

(58) Field of Classification Search
CPC ...... A61K 9/7053; A61K 31/13; A61K 31/27; A61K 31/381; A61K 31/403; A61K 31/407; A61K 31/4422; A61K 31/573
See application file for complete search history.

(56) References Cited

U.S. PATENT DOCUMENTS

| 5,916,587 | A | 6/1999 | Min et al. |
| 2004/0091539 | A1 | 5/2004 | Lindahl et al. |
| 2006/0029654 | A1* | 2/2006 | Cassel .................. A61K 9/7061 424/449 |
| 2009/0137657 | A1* | 5/2009 | Miura .................... A61K 47/10 514/420 |
| 2011/0070296 | A1* | 3/2011 | Lee ........................ A61K 9/006 424/59 |

FOREIGN PATENT DOCUMENTS

| CA | 2633599 A1 * | 7/2007 | ............. A61K 31/00 |
| CN | 107847487 A | 3/2018 | |
| EP | 1869979 A2 * | 12/2007 | ............. A01N 37/12 |
| EP | 3662905 A1 | 6/2020 | |
| JP | H5-186371 A | 7/1993 | |
| JP | 8-53354 A | 2/1996 | |
| JP | H0853354 * | 2/1996 | |
| JP | 2011-241211 A | 12/2011 | |
| JP | 6748237 B2 | 8/2020 | |
| KR | 10-2201003 B1 | 1/2021 | |
| TW | 200538087 A | 12/2005 | |
| WO | WO-2005070887 A1 * | 8/2005 | ........... C07D 217/06 |
| WO | 2007064407 A1 | 6/2007 | |
| WO | 2010098230 A1 | 9/2010 | |
| WO | 2013061969 A1 | 5/2013 | |
| WO | 2015087926 A1 | 6/2015 | |
| WO | 2019026844 A1 | 2/2019 | |

OTHER PUBLICATIONS

"Antipruritic drug Eurax Cream 10%", Nissin Pharmaceutical Co., Ltd., 2018.
Barbaud, A. et al., "Relevance of skin tests with drugs in investigating cutaneous adverse drug reactions", Contact Dermatitis, Jan. 12, 2002, vol. 45, p. 265-p. 268.
International Search Report dated Mar. 24, 2020 corresponding to application No. PCT/JP2020/003491.
International Preliminary Report on Patentability(IPRP) dated Aug. 12, 2021 corresponding to application No. PCT/JP2020/003491.
Taiwan Office Action dated Feb. 14, 2022 corresponding to application No. 109102917.
European Search Report dated Sep. 22, 2022 corresponding to EP Patent Application No. 20749539.1.
Japanese Office Action dated Feb. 15, 2022 corresponding to application No. P2020-568603.
Stefano Veraldi, "Isoconazole nitrate: a unique broad-spectrum antimicrobial azole effective in the treatment of dermatomycoses, both as monotherapy and in combination with corticosteroids", mycoses, Diagnosis, Therapy and Prophylaxis of Fungal Diseases, Blackwell Verlag GmbH, 2013, p. 3-p .15.

* cited by examiner

*Primary Examiner* — Jianfeng Song
(74) *Attorney, Agent, or Firm* — Nath, Goldberg & Meyer; Joshua B. Goldberg

(57) ABSTRACT

The present invention provides a patch comprising an adhesive layer on a backing, wherein the adhesive layer contains a adhesive base, a skin irritant drug or a pharmaceutically acceptable salt thereof, and diflucortolone valerate, and the content of the diflucortolone valerate is 0.0009 to 0.08% by mass based on the total mass of the adhesive layer.

2 Claims, No Drawings

ADHESIVE PATCH

TECHNICAL FIELD

The present invention relates to a patch.

BACKGROUND ART

Since a transdermal formulation such as a patch can deliver a drug directly to blood vessels penetrating the skin, it can avoid disadvantages of oral administration such as degradation by a gastrointestinal enzyme, and the first-pass effect by the liver, and has merits such as reduction of administration frequency, improvement of medication compliance, and easy switching of medication. These merits are especially important when the user is an elderly person or a child.

However, a transdermal formulation causes occasionally symptoms such as pruritus, erythema, eruption, pain, eczema, and dermatitis, (hereinafter also referred to as "skin irritation"). Therefore, various formulations have been studied. For example, as the structure of the patch, a multi-layered patch constituted with a plurality of layers such as a backing layer, a drug retaining layer, and an adhesive layer (see, for example, Patent Literatures 1 and 2), a two-layered patch in which an adhesive layer contains a drug (see, for example, Patent Literature 3) have been proposed.

In the case of the multi-layered patch, the drug retaining layer containing a drug is separated from the skin by the adhesive layer, and even when it is applied to the skin, skin irritation due to a drug is less likely to develop. However, since the total patch thickness of the multi-layered patch increases, there arises a new problem in terms of higher tendency of detachment during use, or adhesion to an inner layer of a preservation package.

CITATION LIST

Patent Literature

[Patent Literature 1] WO 2007/064407
[Patent Literature 2] WO 2015/087926
[Patent Literature 3] WO 2010/098230

SUMMARY OF INVENTION

Technical Problem

Therefore, under such circumstances, an object of the present invention is to provide a patch in which skin irritation and skin atrophy due to the drug are mitigated.

Solution to Problem

[1] A patch comprising an adhesive layer on a backing, wherein the adhesive layer contains an adhesive base, a skin irritant drug or a pharmaceutically acceptable salt thereof, and diflucortolone valerate, and the content of the diflucortolone valerate is 0.0009 to 0.08% by mass based on the total mass of the adhesive layer.
[2] The patch according to [1], wherein the adhesive base comprises at least one adhesive base selected from the group consisting of a rubber based adhesive base, an acrylic adhesive base, and a silicone based adhesive base.
[3-1] The patch according to [1] or [2], wherein the skin irritant drug or a pharmaceutically acceptable salt thereof is asenapine or its pharmaceutically acceptable salt, and the content of the asenapine or its pharmaceutically acceptable salt is 1 to 25% by mass in terms of the mass of free form asenapine based on the total mass of the adhesive layer.
[3-2] The patch according to [1] or [2], wherein the skin irritant drug or a pharmaceutically acceptable salt thereof is rivastigmine, and the content of the rivastigmine is 6 to 30% by mass based on the total mass of the adhesive layer.
[3-3] The patch according to [1] or [2], wherein the skin irritant drug or a pharmaceutically acceptable salt thereof is rotigotine, and the content of the rotigotine is 5 to 15% by mass based on the total mass of the adhesive layer.
[3-4] The patch according to [1] or [2], wherein the skin irritant drug or a pharmaceutically acceptable salt thereof is memantine or its pharmaceutically acceptable salt, and the content of the memantine or its pharmaceutically acceptable salt is 0.1 to 50% by mass in terms of the mass of free form memantine based on the total mass of the adhesive layer.
[3-5] The patch according to [1] or [2], wherein the skin irritant drug or a pharmaceutically acceptable salt thereof is amlodipine or its pharmaceutically acceptable salt, and the content of the amlodipine or its pharmaceutically acceptable salt is 0.1 to 40% by mass in terms of the mass of free form amlodipine based on the total mass of the adhesive layer.
[3-6] The patch according to [1] or [2], wherein the skin irritant drug or a pharmaceutically acceptable salt thereof is ropinirole or its pharmaceutically acceptable salt, and the content of the ropinirole or its pharmaceutically acceptable salt is 0.5 to 50% by mass in terms of the mass of free form ropinirole based on the total mass of the adhesive layer.
[4-1] The patch according to [1], [2], or [3-1], wherein the skin irritant drug or a pharmaceutically acceptable salt thereof is asenapine maleate, and the content of the diflucortolone valerate contained in the adhesive layer is 0.0009 to 0.08% by mass based on the total mass of the adhesive layer.
[4-2] The patch according to [1], [2], or [3-2], wherein the skin irritant drug or a pharmaceutically acceptable salt thereof is rivastigmine, and the content of the diflucortolone valerate contained in the adhesive layer is 0.0009 to 0.08% by mass based on the total mass of the adhesive layer.
[4-3] The patch according to [1], [2], or [3-3], wherein the skin irritant drug or a pharmaceutically acceptable salt thereof is rotigotine, and the content of the diflucortolone valerate contained in the adhesive layer is 0.0005 to 0.08% by mass based on the total mass of the adhesive layer.
[4-4] The patch according to [1], [2], or [3-4], wherein the skin irritant drug or a pharmaceutically acceptable salt thereof is memantine hydrochloride, and the content of the diflucortolone valerate contained in the adhesive layer is 0.0009 to 0.08% by mass based on the total mass of the adhesive layer.
[4-5] The patch according to [1], [2], or [3-5], wherein the skin irritant drug or a pharmaceutically acceptable salt thereof is amlodipine besilate, and the content of the diflucortolone valerate contained in the adhesive layer is 0.0005 to 0.08% by mass based on the total mass of the adhesive layer.
[4-6] The patch according to [1], [2], or [3-6], wherein the skin irritant drug or a pharmaceutically acceptable salt thereof is ropinirole hydrochloride, and the content of the diflucortolone valerate contained in the adhesive layer is 0.0009 to 0.08% by mass based on the total mass of the adhesive layer.
[5-1] The patch according to [1], [2], or [3-1], wherein the skin irritant drug or a pharmaceutically acceptable salt thereof is asenapine maleate, and the mass ratio of asenapine maleate to diflucortolone valerate contained in the adhesive layer is 12.5:1 to 27778:1.

[5-2] The patch according to [1], [2], or [3-2], wherein the skin irritant drug or a pharmaceutically acceptable salt thereof is rivastigmine, and the mass ratio of rivastigmine to diflucortolone valerate contained in the adhesive layer is 75:1 to 33333:1.

[5-3] The patch according to [1], [2], or [3-3], wherein the skin irritant drug or a pharmaceutically acceptable salt thereof is rotigotine, and the mass ratio of rotigotine to diflucortolone valerate contained in the adhesive layer is 62.5:1 to 20000:1.

[5-4] The patch according to [1], [2], or [3-4], wherein the skin irritant drug or a pharmaceutically acceptable salt thereof is memantine hydrochloride, and the mass ratio of memantine hydrochloride to diflucortolone valerate contained in the adhesive layer is 1.25:1 to 55556:1.

[5-5] The patch according to [1], [2], or [3-5], wherein the skin irritant drug or a pharmaceutically acceptable salt thereof is amlodipine besilate, and the mass ratio of amlodipine besilate to diflucortolone valerate contained in the adhesive layer is 1.25:1 to 44444:1.

[5-6] The patch according to [1], [2], or [3-6], wherein the skin irritant drug or a pharmaceutically acceptable salt thereof is ropinirole hydrochloride, and the mass ratio of ropinirole hydrochloride to diflucortolone valerate contained in the adhesive layer is 6.25:1 to 55556:1.

Advantageous Effects of Invention

According to the present invention, it is possible to provide a patch in which skin irritation and skin atrophy due to the drug are mitigated.

DESCRIPTION OF EMBODIMENTS

The term "skin irritation" means herein a skin irritation to develop at an application site, when a patch containing an optional drug is applied to the skin, and includes specifically skin symptom, such as pruritus, erythema, eruption, pain, eczema, and dermatitis. In this regard, the severity of skin irritation can be evaluated based on the scores given corresponding to the severity of erythema and edema as the criteria.

The term "skin atrophy" means herein a symptom in which, when a steroid is applied to the skin, the epidermis of the application site becomes thinner than the normal epidermis (the thickness of the epidermis in a state not affected by the steroid). The severity of skin atrophy can be judged by the criterion whether or not the thickness of the epidermis after an application of a patch to the skin is 50% or less as compared with the thickness of the normal epidermis.

"Mitigation of skin irritation" and "mitigation of skin atrophy" in the present invention are relatively evaluated by, for example, the method described in Examples.

The patch according to an Embodiment of the present invention is a patch comprising an adhesive layer on a backing, wherein the adhesive layer contains an adhesive base, a skin irritant drug or a pharmaceutically acceptable salt thereof, and diflucortolone valerate.

The backing is a layer that physically supports the adhesive layer. There is no particular restriction on the material of the backing, insofar as it is generally used for a patch. Examples of the material of the backing include polyolefins such as polyethylene, polypropylene, and polybutadiene; polyesters such as poly(ethylene terephthalate), poly(butylene terephthalate) and poly(ethylene naphthalate); and synthetic resins such as an ethylene/vinyl acetate copolymer, a vinyl acetate/vinyl chloride copolymer, poly(vinyl chloride), polyamide, nylon, cellulose derivatives, and polyurethane. The form of the backing may be a film, a sheet, a sheet-like porous body, a sheet-like foamed body, a woven fabric, a knitted fabric, a nonwoven fabric, or a laminate thereof.

The adhesive layer contains an adhesive base, a skin irritant drug or a pharmaceutically acceptable salt thereof, and diflucortolone valerate. However, the skin irritant drug herein is not oxybutynin.

There is no particular restriction on the adhesive base, insofar as it is used generally for a patch, and examples thereof include a rubber based adhesive base, an acrylic adhesive base, and a silicone based adhesive base. A plurality of adhesive bases may be used in combination. A preferable adhesive base is a rubber based adhesive base, an acrylic adhesive base, or a mixture of them.

The rubber based adhesive base may be a polymer composed mainly of a natural or synthetic rubber, and examples thereof include polyisoprene, polyisobutylene, polybutadiene, a styrene/isoprene/styrene block copolymer (SIS block copolymer), a styrene/butadiene/styrene block copolymer, a styrene/butadiene rubber, and a styrene/isoprene rubber.

Examples of the acrylic adhesive base include a polymer of an alkyl (meth)acrylate, and a copolymer of an alkyl (meth)acrylate and a comonomer. Here, "(meth)acrylic acid", and similar expressions mean acrylic acid, methacrylic acid, or both, and the alkyl group is an alkyl group having 1 to 20 carbon atoms, and is preferably an alkyl group having 3 to 12 carbon atoms. Examples of the alkyl (meth)acrylate include butyl (meth)acrylate, isobutyl (meth)acrylate, hexyl (meth)acrylate, octyl (meth)acrylate, 2-ethylhexyl (meth)acrylate, and decyl (meth)acrylate. The alkyl (meth)acrylates may be used singly or in combinations of two or more thereof. Examples of the comonomer include a hydroxyalkyl (meth)acrylate, ethylene, propylene, styrene, vinyl acetate, N-vinylpyrrolidone, and (meth)acrylic acid amide. These comonomers may be used singly or in combinations of two or more thereof. Specific examples of the acrylic adhesive base include copolymers containing at least two selected from butyl acrylate, 2-ethylhexyl acrylate, vinyl acetate, methacrylic acid, hydroxyethyl acrylate, glycidyl methacrylate, methoxyethyl acrylate, and acrylic acid. Specific examples include DURO-TAK 87-2097, 87-2194, 87-2196, 87-2287, 87-2516, and 87-2852 (trade names, Henkel AG & Co.), MAS811 (trade name, produced by CosMED Pharmaceutical Co. Ltd.), PLASTOID B (trade name, produced by Rohm Pharm Polymers), and NISSETSU KP-77 and AS-370 (trade names, Nippon Carbide Industries Co., Inc.).

The acrylic adhesive base may be an acrylic adhesive base having no functional group, or may be an acrylic adhesive base having a functional group. The "functional group" means a group having an element other than a carbon atom and a hydrogen atom, and examples thereof include a hydroxy group, an alkoxy group, a carboxy group (including a salt), a 2-oxopyrrolidinyl group, an acetoxy group, an amide group, a glycidyl group, an amino group, a monoalkylamino group, a dialkylamino group, and a quaternary ammonium. Such a functional group is mainly derived from the chemical structure of a comonomer.

Examples of the silicone based adhesive base include organopolysiloxanes, such as dimethylpolysiloxanes, and condensation reaction products of a dimethylpolysiloxane and a silicate resin. Specific examples of the silicone based adhesive base include BIO-PSA X7-4201, BIO-PSA Q7-4501, 360Medical fluid 1000CS, and MDX 4-4210 (trade names, Dow Corning Corp.).

The content of the adhesive base is preferably 5 to 90% by mass, for example, based on the total mass of the adhesive layer, more preferably 10 to 50% by mass, and further preferably 10 to 30% by mass.

There is no particular restriction on the skin irritant drug, insofar as it is a drug (free form) exhibiting dermal irritancy and transdermal absorption capability. The "skin irritant drug or a pharmaceutically acceptable salt thereof" in the present invention means a drug which wins an average score of 0.1 to 2.0 according to the severity criteria of Draize, et al. (Reference: Draize J H, et al., J. Pharmacol. Exp. Ther., 1944:82: 377-390) at 0.5 hour after the patch is removed which has been applied to a HWY/Slc rat as described below in a Test example 1.

Examples of the skin irritant drug or a pharmaceutically acceptable salt thereof include an antipyretic antiphlogistic analgesic (e.g. indomethacin), an anti-inflammatory drug (e.g. capsaicin, and red pepper extract), a drug for psycho neurosis (e.g. citalopram hydrobromide, asenapine maleate, and risperidone), a local anesthetic (e.g. lidocaine hydrochloride), a drug for urinary organs (e.g. tolterodine), an anti-Parkinson's disease drug (e.g. ropinirole hydrochloride, and rotigotine), an anti-smoking aid (e.g. nicotine), a drug for circulatory organs (e.g. amlodipine besilate), an antiallergic drug (e.g. ketotifen fumarate), an anti-Alzheimer's dementia drug (e.g. donepezil hydrochloride, rivastigmine, and memantine hydrochloride), a skeletal muscle relaxant (e.g. tizanidine hydrochloride), a prostacyclin receptor agonist (e.g. selexipag), and a stimulant (e.g. methamphetamine hydrochloride, and methylphenidate hydrochloride). These drugs or pharmaceutically acceptable salts thereof may be solely a free form of the drug, solely a pharmaceutically acceptable salt thereof, or their mixture.

The content of a skin irritant drug or a pharmaceutically acceptable salt thereof may be an amount that can ensure an effective blood concentration of the drug. When the content of a skin irritant drug is less than the lower limit of the specified range, the area of the patch needs to be increased because the skin permeation amount tends to decrease; meanwhile, when it exceeds the upper limit, local side effects such as skin irritation may occur, or the adhesive properties such as the adhesion to the skin, or the tackiness may be deteriorated.

When the pharmaceutically acceptable salt of a skin irritant drug is asenapine maleate, its content may be in terms of the mass of free form asenapine based on the total mass of the adhesive layer 1 to 25% by mass, 1 to 15% by mass, 1.5 to 12% by mass, 2 to 10% by mass, 3 to 8% by mass, or 4 to 7% by mass.

When the skin irritant drug is rivastigmine, its content may be based on the total mass of the adhesive layer 6 to 30% by mass, 10 to 30% by mass, or 20 to 30% by mass.

When the skin irritant drug is rotigotine, its content may be based on the total mass of the adhesive layer 5 to 15% by mass, 7 to 12% by mass, or 8 to 10% by mass.

When the pharmaceutically acceptable salt of a skin irritant drug is memantine hydrochloride, its content may be in terms of the mass of free form memantine based on the total mass of the adhesive layer 0.1 to 50% by mass, 5 to 45% by mass, 10 to 40% by mass, 10 to 30% by mass, 11 to 20% by mass, or 12 to 15% by mass.

When the pharmaceutically acceptable salt of a skin irritant drug is amlodipine besilate, its content may be in terms of the mass of free form amlodipine based on the total mass of the adhesive layer 0.1 to 40% by mass, 0.2 to 30% by mass, 0.5 to 20% by mass, 0.6 to 10% by mass, 0.8 to 8% by mass, or 1 to 5% by mass.

When the pharmaceutically acceptable salt of a skin irritant drug is ropinirole hydrochloride, its content may be in terms of the mass of free form ropinirole based on the total mass of the adhesive layer 0.5 to 50% by mass, 5 to 30% by mass, 10 to 20% by mass, or 12 to 20% by mass.

Diflucortolone valerate is also called 6α,9-difluoro-11β-hydroxy-21-valeryloxy-16α-methyl-1,4-pregnadiene-3,20-dione. Diflucortolone valerate is a kind of steroid having a synthetic adrenocortical hormone effect, and has an anti-inflammatory effect similar to other steroids. According to Japanese atopic dermatitis clinical practice guideline 2018, diflucortolone valerate belongs to Class II (very strong) out of 5 classifications of steroids.

The content of diflucortolone valerate is required to be 0.0009 to 0.08% by mass based on the total mass of the adhesive layer, and is preferably 0.0009 to 0.05% by mass. When the content of diflucortolone valerate is 0.0009% by mass or more, it tends to become easier to alleviate skin irritation of the drug. When the content of diflucortolone valerate is 0.08% by mass or less, skin atrophy at an application site becomes less likely to occur.

When the pharmaceutically acceptable salt of a skin irritant drug is asenapine maleate, the content of diflucortolone valerate is required to be 0.0009 to 0.08% by mass based on the total mass of the adhesive layer, and is preferably 0.0009 to 0.05% by mass. When the content of diflucortolone valerate is 0.0009% by mass or more, it tends to become easier to alleviate skin irritation of the drug. When the content of diflucortolone valerate is 0.08% by mass or less, skin atrophy at an application site becomes less likely to occur.

When the skin irritant drug is rivastigmine, the content of diflucortolone valerate is required to be 0.0009 to 0.08% by mass based on the total mass of the adhesive layer, and is preferably 0.0009 to 0.05% by mass. When the content of diflucortolone valerate is 0.0009% by mass or more, it tends to become easier to alleviate skin irritation of the drug. When the content of diflucortolone valerate is 0.08% by mass or less, skin atrophy at an application site becomes less likely to occur.

When the skin irritant drug is rotigotine, the content of diflucortolone valerate is required to be 0.0005 to 0.08% by mass based on the total mass of the adhesive layer, and is preferably 0.0005 to 0.05% by mass. When the content of diflucortolone valerate is 0.0005% by mass or more, it tends to become easier to alleviate skin irritation of the drug. When the content of diflucortolone valerate is 0.08% by mass or less, skin atrophy at an application site becomes less likely to occur.

When the pharmaceutically acceptable salt of a skin irritant drug is memantine hydrochloride, the content of diflucortolone valerate is required to be 0.0009 to 0.08% by mass based on the total mass of the adhesive layer, and is preferably 0.0009 to 0.05% by mass. When the content of diflucortolone valerate is 0.0009% by mass or more, it tends to become easier to alleviate skin irritation of the drug. When the content of diflucortolone valerate is 0.08% by mass or less, skin atrophy at an application site becomes less likely to occur.

When the pharmaceutically acceptable salt of a skin irritant drug is amlodipine besilate, the content of diflucortolone valerate is required to be 0.0005 to 0.08% by mass based on the total mass of the adhesive layer, and is preferably 0.0005 to 0.05% by mass. When the content of diflucortolone valerate is 0.0005% by mass or more, it tends to become easier to alleviate skin irritation of the drug. When the content of diflucortolone valerate is 0.08% by mass or less, skin atrophy at an application site becomes less likely to occur.

When the pharmaceutically acceptable salt of a skin irritant drug is ropinirole hydrochloride, the content of diflucortolone valerate is required to be 0.0009 to 0.08% by mass based on the total mass of the adhesive layer, and is preferably 0.0009 to 0.05% by mass. When the content of diflucortolone valerate is 0.0009% by mass or more, it tends to become easier to alleviate skin irritation of the drug. When the content of diflucortolone valerate is 0.08% by mass or less, skin atrophy at an application site becomes less likely to occur.

Further, the mass ratio of a skin irritant drug to diflucortolone valerate contained in the adhesive layer is preferably in the following range. When the adhesive layer contains a pharmaceutically acceptable salt of a skin irritant drug, for the content of the salt in terms of the mass of the free form of the drug based on the molecular weight of the entire salt, the mass ratio between the free form and the diflucortolone valerate is calculated.

When the pharmaceutically acceptable salt of a skin irritant drug is asenapine maleate, the mass ratio of asenapine maleate (in terms of the mass of free form asenapine) to diflucortolone valerate contained in the adhesive layer is preferably 12.5:1 to 27778:1, 12.5:1 to 16667:1, 18.75:1 to 13333:1, 40:1 to 10000:1, 70:1 to 9000:1, 100:1 to 8000:1, or 110:1 to 7000:1.

When the skin irritant drug is rivastigmine, the mass ratio of rivastigmine to diflucortolone valerate contained in the adhesive layer is preferably 75:1 to 33333:1, 125:1 to 33333:1, 300:1 to 30000:1, 400:1 to 30000:1, or 400:1 to 26000:1.

When the skin irritant drug is rotigotine, the mass ratio of rotigotine to diflucortolone valerate contained in the adhesive layer is preferably 62.5:1 to 20000:1, 62.5:1 to 18000:1, 62.5:1 to 16667:1, 87.5:1 to 13333:1, 100:1 to 12000:1, 150:1 to 11000:1, or 160:1 to 10000:1.

When the pharmaceutically acceptable salt of a skin irritant drug is memantine hydrochloride, the mass ratio of memantine hydrochloride (in terms of the mass of free form memantine) to diflucortolone valerate contained in the adhesive layer is preferably 1.25:1 to 55556:1, 62.5:1 to 50000:1, 140:1 to 45000:1, 200:1 to 40000:1, 220:1 to 25000:1, or 250:1 to 15000:1.

When the pharmaceutically acceptable salt of a skin irritant drug is amlodipine besilate, the mass ratio of amlodipine besilate (in terms of the mass of free form amlodipine) to diflucortolone valerate contained in the adhesive layer is preferably 1.25:1 to 44444:1, 6.25:1 to 22222:1, 20:1 to 5000:1, 20:1 to 2000:1, or 20:1 to 1600:1.

When the pharmaceutically acceptable salt of a skin irritant drug is ropinirole hydrochloride, the mass ratio of ropinirole hydrochloride (in terms of the mass of free form ropinirole) to diflucortolone valerate contained in the adhesive layer is preferably 6.25:1 to 55556:1, 62.5:1 to 33333:1, 200:1 to 30000:1, or 200:1 to 15000:1.

The adhesive layer may additionally contain another component (such as a tackifier, a plasticizer, a filler, a stabilizer, a drug penetration enhancer, and a perfume).

Examples of the tackifier include a terpene resin, a terpene phenol resin, a rosin ester resin, a hydrogenated rosin ester resin, an alicyclic saturated hydrocarbon resin, and a petroleum resin. The terpene resin is preferably a hydrogenated terpene resin. Examples of the terpene resin include an α-pinene resin, a β-pinene resin, an aromatic modified terpene resin, and a terpene phenol resin.

Examples of the plasticizer include paraffin oil (such as liquid paraffin), squalane, squalene, vegetable oils (such as olive oil, camellia oil, castor oil, tall oil, peanut oil, spearmint oil, eucalyptus oil, jojoba oil, white camphor oil, sunflower oil, and orange oil), esters (such as dibutyl phthalate, and dioctyl phthalate), and liquid rubber (such as liquid polybutene, and liquid isoprene rubber).

Examples of the filler include powders of a metal compound (such as aluminum oxide, aluminum hydroxide, zinc oxide, titanium oxide, and calcium carbonate), ceramics (such as talc, clay, kaolin, silica, hydroxyapatite, synthetic aluminum silicate, and magnesium aluminometasilicate), or an organic compound (such as cellulose powder, and stearates), and short fibers of a resin containing the above.

As the penetration enhancer any compound heretofore known to have a penetration enhancing effect in the skin may be used. Examples of the penetration enhancer include organic acids and salts thereof (such as aliphatic carboxylic acids having 6 to 20 carbon atoms (hereinafter also referred to as "fatty acids") and salts thereof, as well as cinnamic acid and salts thereof), organic acid esters (such as fatty acid esters, and cinnamic acid esters), organic acid amides (such as fatty acid amides), fatty alcohols, polyhydric alcohols, ethers (such as fatty ethers, and polyoxyethylene alkyl ethers). These absorption enhancers may have an unsaturated bond, and may have a cyclic, linear, or branched chemical structure. The penetration enhancer may also be a monoterpene compound, a sesquiterpene compound, or a vegetable oil (such as olive oil). The penetration enhancers may be used singly, or in combinations of two or more thereof.

Examples of the organic acid include aliphatic (mono, di, or tri) carboxylic acids (such as acetic acid, propionic acid, citric acid (including anhydrous citric acid), isobutyric acid, caproic acid, caprylic acid, fatty acids, lactic acid, maleic acid, pyruvic acid, oxalic acid, succinic acid, and tartaric acid), aromatic carboxylic acids (such as phthalic acid, salicylic acid, benzoic acid, and acetylsalicylic acid), cinnamic acid, alkanesulfonic acids (such as methanesulfonic acid, ethanesulfonic acid, propanesulfonic acid, and butanesulfonic acid), alkylsulfonic acid derivatives (such as a polyoxyethylene alkyl ether sulfonic acid, N-2-hydroxyethylpiperazine-N'-2-ethanesulfonic acid), cholic acid derivatives (such as dehydrocholic acid). These organic acids may be alkali metal salts such as sodium salts. Among them, aliphatic carboxylic acids, aromatic carboxylic acids, or salts thereof are preferable, and acetic acid, sodium acetate, or citric acid is particularly preferable.

Examples of the fatty acid include lauric acid, myristic acid, palmitic acid, stearic acid, isostearic acid, oleic acid, linoleic acid, and linolenic acid.

Examples of the organic acid ester include ethyl acetate, propyl acetate, cetyl lactate, lauryl lactate, methyl salicylate, ethylene glycol salicylate, methyl cinnamate, and fatty acid esters. Examples of the fatty acid ester include methyl laurate, hexyl laurate, isopropyl myristate, myristyl myristate, octyldodecyl myristate, and cetyl palmitate. The fatty acid ester may be also glycerol fatty acid ester, propylene glycol fatty acid ester, sorbitan fatty acid ester, polyethylene glycol sorbitan fatty acid ester, polyethylene glycol fatty acid ester, sucrose fatty acid ester, or polyoxyethylene hydrogenated castor oil. Specific examples of the fatty acid ester include glycerol monocaprylate, glycerol monocaprate, glycerol monolaurate, glycerol monooleate, sorbitan monolaurate, sucrose monolaurate, Polysorbate 20

(trade name), propylene glycol monolaurate, polyethylene glycol monolaurate, polyethylene glycol monostearate, Span 20, Span 40, Span 60, Span 80, Span 120 (trade names), Tween 20, Tween 21, Tween 40, Tween 60, Tween 80 (trade names), and NIKKOL HCO-60 (trade name).

Examples of the organic acid amide include fatty acid amides (such as lauric acid diethanolamide), hexahydro-1-dodecyl-2H-azepin-2-one (also called Azone) and its derivatives, and pyrrothiodecane.

Fatty alcohol means an aliphatic alcohol having 6 to 20 carbon atoms. Examples of the fatty alcohol include lauryl alcohol, myristyl alcohol, oleyl alcohol, isostearyl alcohol, and cetyl alcohol. Examples of the polyhydric alcohol include propylene glycol.

Examples of the polyoxyethylene alkyl ether include polyoxyethylene lauryl ether.

Examples of the monoterpene compound include geraniol, thymol, eugenol, terpineol, 1-menthol, borneol, d-limonene, isoeugenol, isoborneol, nerol, and dl-camphor.

More preferable is oleyl alcohol, lauryl alcohol, isostearyl alcohol, lauric acid diethanolamide, glycerol monocaprylate, glycerol monocaprate, glycerol monooleate, sorbitan monolaurate, propylene glycol monolaurate, polyoxyethylene lauryl ether, or pyrrothiodecane. Fatty acids are preferred, and oleic acid is particularly preferable.

The adhesive layer may be provided with a release liner on the side which is opposite to the backing and comes into contact with the skin. The release liner is a liner to be removed when the patch is used, and is not particularly restricted insofar as it is generally used for a patch. Examples of the material for the release liner include polyester (such as poly(ethylene terephthalate) (PET)), polyolefin (such as polypropylene, and polyethylene), cellulose compounds (such as paper). The release liner may be in the form of a sheet consisting of a laminate of the above materials. It is preferable that the surface of the release liner is release-treated with a silicone, a fluorinated polyolefin, or the like.

The patch according to this Embodiment can be produced, for example, by the following method.
1) The ingredients of an adhesive layer are weighed out, then, if necessary, heating and addition of a solvent are performed, and the mixture is mixed to be homogenized.
2) The obtained adhesive composition is spread over the release surface of a release liner at a constant thickness, and, if necessary, dried to remove the solvent component to form an adhesive layer.
3) The backing is layered on the adhesive layer.
4) The laminate is cut into a predetermined shape (for example, a rectangle having a short side of 3 cm to 14 cm, and a long side of 7 cm to 20 cm, or a circle having a diameter of 1 cm to 10 cm).

EXAMPLES

The patch of the present invention will be described below in more detail using Examples and Comparative Examples.
<Production of Patch>
According to the description in each table, predetermined amounts of the respective ingredients were mixed to prepare a uniform adhesive composition. The prepared adhesive composition was spread over a film (release liner) made of poly(ethylene terephthalate) to form an adhesive layer. A poly(ethylene terephthalate) film (backing) was laminated on the adhesive layer, and the laminate was cut into a predetermined shape to yield a patch of Example, Comparative Example, or Reference Example. In each table, the numerical values are expressed in % by mass, unless otherwise specified.

Test Example 1: Evaluations of Skin Irritation and Skin Atrophy

HWY: Slc rats (6 to 7 weeks-old, female) were purchased and acclimated for not less than 6 days. During the acclimation period, the hairs on the back of the rat were clipped and shaved. Rats in good general condition and skin condition were selected from all the rats, and grouping was performed to form groups consisting of even body weight rats. Any one of the patches and the patch of Comparative Example 1 as the control were applied to each group of rats. Specifically, on the day of application, an application site (about 1.5 cm×1.5 cm or about 1 cm×1 cm rectangle) was set on the skin of the rat back (shaved region) and its four corners were marked. The patches obtained above were applied on to the marked application sites, respectively. After application, a mesh adhesive bandage was bonded so as to cover the application site, which was further covered with a lint cloth, and fixed with an adhesive elastic bandage. The lint cloth, adhesive bandage and patch were removed 24 hours after the application, and the severity of skin irritation was evaluated with respect to the rats in each group. After the evaluation of the severity of skin irritation, the skin at the application site was excised to prepare a skin section sample, and the severity of skin atrophy was evaluated.

The evaluation of skin irritation was carried out based on the severity criteria of Draize, et al. (reference: Draize J H, et al., J. Pharmacol. Exp. Ther., 1944:82:377-390) 0.5 hour after removal of the patch. Specifically, by observing the skin of the application site after 0.5 hour from peeling, scores were given with respect to (1) erythema and eschar formation, and (2) edema formation according to the following criteria, and the average value was calculated for each group. Then a relative value of the average score of an Example with respect to the average score of the corresponding Reference Example (patch not containing a steroid drug) was calculated. In other words, the severity of skin irritation was recorded as a relative value with respect to the average score of the patch of the corresponding Reference Example.

When the average score of an Example or a Comparative Example was 60% or less with reference to the average score of the corresponding Reference Example, it was rated as "A", and when it exceeded 60%, it was rated as "B".
<Severity Criteria of Draize, et al.>
(1) Erythema and eschar formation
  0: No erythema
  1: Very slight erythema (barely perceptible)
  2: Well-defined erythema
  3: Moderate to severe erythema
  4: Severe erythema (beet redness) to slight eschar formation (injuries at depth)
(2) Edema formation
  0: No edema
  1: Very slight edema (barely perceptible)
  2: Slight edema (edges of area well defined by definite raising)
  3: Moderate edema (raised approximately about 1 mm)
  4: Severe edema (raised more than 1 mm and extending beyond area of exposure)

The evaluation of skin atrophy was performed on rats (2 animals in each group) having undergone the evaluation of skin irritation. Whole blood was collected from the abdominal aorta of each animal under anesthesia by inhalation of isoflurane. After blood collection, a section of epidermis of the skin including each application site was sampled, and the obtained epidermis section was fixed with a 10% formalin solution. The central portion of the application site of the epidermis section after fixation was cut out, embedded in paraffin, and stained with hematoxylin and eosin (HE staining), and the obtained sample was observed with a microscope (trade name: BX50, manufactured by Olympus Corporation). An image of the sample photographed with a microscope was analyzed using an image analysis software (trade name: WinROOF ver. 7.3, produced by Mitani Corporation), and the thickness of the epidermis was measured. For each epidermis section, the thickness of the epidermis was measured at five positions, and the average value was calculated.

In a case where the thickness of the epidermis in the application site exceeded 50% of the thickness of the epidermis at the site without application (normal skin), it was rated as "A", and in a case where the same was 50% or less, it was rated as "B".

With respect to the patches containing asenapine maleate, the results of Tests 1 to 6 are shown in Tables 1 and 2. The patch of Comparative Example 1 could not sufficiently alleviate the skin irritation caused by asenapine maleate. With the patch of Comparative Example 2, skin atrophy was recognized.

With respect to the patches containing rotigotine, the results of Tests 7 to 10 are shown in Tables 3 and 4. With the patch of Comparative Example 3, skin atrophy was recognized.

TABLE 3

|  | Test 7 | | Test 8 | |
|---|---|---|---|---|
|  | Ex. 5 | Ref. Ex. 2 | Ex. 6 | Ref. Ex. 3 |
| Rotigotine | 9.00 | 9.00 | 9.00 | 9.00 |
| SIS BLOCK COPOLYMER | 12.19 | 12.19 | 13.6 | 13.6 |
| Polyisobutylene | 5.23 | 5.23 | 5.82 | 5.82 |
| Alicyclic saturated hydrocarbon resin | 44.3791 | 44.38 | 42.725 | 42.73 |
| Liquid paraffin | 13.93 | 13.93 | 15.54 | 15.54 |
| Octyldodecanol | 5.00 | 5.00 | 3.00 | 3.00 |
| Crospovidone | 10.00 | 10.00 | 10.00 | 10.00 |
| Diflucortolone valerate | 0.0009 | 0 | 0.005 | 0 |
| Other ingredients | 0.27 | 0.27 | 0.31 | 0.31 |
| Total | 100.00 | 100.00 | 100.00 | 100.00 |
| Skin irritation | A | — | A | — |
| Skin atrophy | A | A | A | A |

TABLE 1

|  | Test 1 | | Test 2 | | Test 3 | |
|---|---|---|---|---|---|---|
|  | Comp. Ex. 1 | Ref. Ex. 1 | Ex. 1 | Ref. Ex. 1 | Ex. 2 | Ref. Ex. 1 |
| Asenapine maleate | 9.00 | 9.00 | 9.00 | 9.00 | 9.00 | 9.00 |
| SIS BLOCK COPOLYMER | 11.95 | 11.95 | 11.95 | 11.95 | 11.95 | 11.95 |
| Alicyclic saturated hydrocarbon resin | 49.4993 | 49.5 | 49.499 | 49.5 | 49.4975 | 49.5 |
| Liquid paraffin | 6.83 | 6.83 | 6.83 | 6.83 | 6.83 | 6.83 |
| Sodium acetate | 7.35 | 7.35 | 7.35 | 7.35 | 7.35 | 7.35 |
| Diflucortolone valerate | 0.0007 | 0 | 0.001 | 0 | 0.0025 | 0 |
| Other ingredients | 15.37 | 15.37 | 15.37 | 15.37 | 15.37 | 15.37 |
| Total | 100.00 | 100.00 | 100.00 | 100.00 | 100.00 | 100.00 |
| Skin irritation | B | — | A | — | A | — |
| Skin atrophy | A | A | A | A | A | A |

TABLE 2

|  | Test 4 | | Test 5 | | Test 6 | |
|---|---|---|---|---|---|---|
|  | Ex. 3 | Ref. Ex. 1 | Ex. 4 | Ref. Ex. 1 | Comp. Ex. 2 | Ref. Ex. 1 |
| Asenapine maleate | 9.00 | 9.00 | 9.00 | 9.00 | 9.00 | 9.00 |
| SIS BLOCK COPOLYMER | 11.95 | 11.95 | 11.94 | 11.95 | 11.93 | 11.95 |
| Alicyclic saturated hydrocarbon resin | 49.495 | 49.5 | 49.47 | 49.5 | 49.43 | 49.5 |
| Liquid paraffin | 6.83 | 6.83 | 6.82 | 6.83 | 6.82 | 6.83 |
| Sodium acetate | 7.35 | 7.35 | 7.35 | 7.35 | 7.35 | 7.35 |
| Diflucortolone valerate | 0.005 | 0 | 0.05 | 0 | 0.10 | 0 |
| Other ingredients | 15.37 | 15.37 | 15.37 | 15.37 | 15.37 | 15.37 |
| Total | 100.00 | 100.00 | 100.00 | 100.00 | 100.00 | 100.00 |
| Skin irritation | A | — | A | — | A | — |
| Skin atrophy | A | A | A | A | B | A |

TABLE 4

|  | Test 9 | | Test 10 | |
| --- | --- | --- | --- | --- |
|  | Ex. 7 | Ref. Ex. 4 | Comp. Ex. 3 | Ref. Ex. 5 |
| Rotigotine | 9.00 | 9.00 | 9.00 | 9.00 |
| SIS BLOCK COPOLYMER | 12.18 | 12.19 | 13.58 | 13.60 |
| Polyisobutylene | 5.22 | 5.23 | 5.82 | 5.82 |
| Alicyclic saturated hydrocarbon resin | 44.36 | 44.38 | 42.67 | 42.73 |
| Liquid paraffin | 13.92 | 13.93 | 15.52 | 15.54 |
| Octyldodecanol | 5.00 | 5.00 | 3.00 | 3.00 |
| Crospovidone | 10.00 | 10.00 | 10.00 | 10.00 |
| Diflucortolone valerate | 0.05 | 0 | 0.10 | 0 |
| Other ingredients | 0.27 | 0.27 | 0.31 | 0.31 |
| Total | 100.00 | 100.00 | 100.00 | 100.00 |
| Skin irritation | A | — | A | — |
| Skin atrophy | A | A | B | A |

With respect to the patches containing rotigotine, the results of Test 33 are shown in Table 5.

TABLE 5

|  | Test 33 | | |
| --- | --- | --- | --- |
|  | Ex. 26 | Ex. 27 | Ref. Ex. 2 |
| Rotigotine | 9 | 9 | 9 |
| SIS BLOCK COPOLYMER | 12.19 | 12.19 | 12.19 |
| Polyisobutylene | 5.23 | 5.23 | 5.23 |
| Alicyclic saturated hydrocarbon resin | 44.3795 | 44.3793 | 44.38 |
| Liquid paraffin | 13.93 | 13.93 | 13.93 |
| Octyldodecanol | 5 | 5 | 5 |
| Crospovidone | 10 | 10 | 10 |
| Diflucortolone valerate | 0.0005 | 0.0007 | 0 |
| Other ingredients | 0.27 | 0.27 | 0.27 |
| Total | 100 | 100 | 100 |
| Skin irritation | A | A | — |
| Skin atrophy | A | A | A |

With respect to the patches containing rivastigmine, the results of Tests 11 to 16 are shown in Tables 6 and 7. The acrylic adhesive base X is an acrylic adhesive base having no functional group, and the acrylic adhesive base Y is an acrylic adhesive base having a carboxy group. With the patch of Comparative Example 4, skin atrophy was recognized.

TABLE 6

|  | Test 11 | | Test 12 | | Test 13 | |
| --- | --- | --- | --- | --- | --- | --- |
|  | Ex. 8 | Ref. Ex. 6 | Ex. 9 | Ref. Ex. 6 | Ex. 10 | Ref. Ex. 6 |
| Rivastigmine | 25.00 | 25.00 | 25.00 | 25.00 | 25.00 | 25.00 |
| Acrylic adhesive base X | 33.4995 | 33.5 | 33.49875 | 33.5 | 33.4975 | 33.5 |
| Acrylic adhesive base Y | 33.4995 | 33.5 | 33.49875 | 33.5 | 33.4975 | 33.5 |
| PLASTOID B | 7.00 | 7.00 | 7.00 | 7.00 | 7.00 | 7.00 |
| Diflucortolone valerate | 0.001 | 0 | 0.0025 | 0 | 0.005 | 0 |
| Other ingredients | 1.00 | 1.00 | 1.00 | 1.00 | 1.00 | 1.00 |
| Total | 100.00 | 100.00 | 100.00 | 100.00 | 100.00 | 100.00 |
| Skin irritation | A | — | A | — | A | — |
| Skin atrophy | A | A | A | A | A | A |

TABLE 7

|  | Test 14 | | Test 15 | | Test 16 | |
| --- | --- | --- | --- | --- | --- | --- |
|  | Ex. 11 | Ref. Ex. 6 | Ex. 12 | Ref. Ex. 6 | Comp. Ex. 4 | Ref. Ex. 6 |
| Rivastigmine | 25.00 | 25.00 | 25.00 | 25.00 | 25.00 | 25.00 |
| Acrylic adhesive base X | 33.4875 | 33.5 | 33.475 | 33.5 | 33.45 | 33.5 |
| Acrylic adhesive base Y | 33.4875 | 33.5 | 33.475 | 33.5 | 33.45 | 33.5 |
| PLASTOID B | 7.00 | 7.00 | 7.00 | 7.00 | 7.00 | 7.00 |
| Diflucortolone valerate | 0.025 | 0 | 0.05 | 0 | 0.10 | 0 |
| Other ingredients | 1.00 | 1.00 | 1.00 | 1.00 | 1.00 | 1.00 |
| Total | 100.00 | 100.00 | 100.00 | 100.00 | 100.00 | 100.00 |
| Skin irritation | A | — | A | — | A | — |
| Skin atrophy | A | A | A | A | B | A |

With respect to the patches containing memantine hydrochloride, the results of Tests 17 to 20 are shown in Tables 8 and 9. With the patch of Comparative Example 5, skin atrophy was recognized.

TABLE 8

|  | Test 17 | | Test 18 | |
|---|---|---|---|---|
|  | Ex. 13 | Ref. Ex. 7 | Ex. 14 | Ref. Ex. 7 |
| Memantine hydrochloride | 16.00 | 16.00 | 16.00 | 16.00 |
| SIS BLOCK COPOLYMER | 13.24 | 13.24 | 13.24 | 13.24 |
| Polyisobutylene | 5.67 | 5.67 | 5.67 | 5.67 |
| Alicyclic saturated hydrocarbon resin | 32.139 | 32.14 | 32.135 | 32.14 |
| Liquid paraffin | 22.69 | 22.69 | 22.69 | 22.69 |
| Sodium hydroxide | 3.26 | 3.26 | 3.26 | 3.26 |
| Diflucortolone valerate | 0.001 | 0 | 0.005 | 0 |
| Other ingredients | 7.00 | 7.00 | 7.00 | 7.00 |
| Total | 100.00 | 100.00 | 100.00 | 100.00 |
| Skin irritation | A | — | A | — |
| Skin atrophy | A | A | A | A |

TABLE 9

|  | Test 19 | | Test 20 | |
|---|---|---|---|---|
|  | Ex. 15 | Ref. Ex. 7 | Comp. Ex. 5 | Ref. Ex. 7 |
| Memantine hydrochloride | 16.00 | 16.00 | 16.00 | 16.00 |
| SIS BLOCK COPOLYMER | 13.23 | 13.24 | 13.22 | 13.24 |
| Polyisobutylene | 5.67 | 5.67 | 5.67 | 5.67 |
| Alicyclic saturated hydrocarbon resin | 32.12 | 32.14 | 32.09 | 32.14 |
| Liquid paraffin | 22.67 | 22.69 | 22.66 | 22.69 |
| Sodium hydroxide | 3.26 | 3.26 | 3.26 | 3.26 |
| Diflucortolone valerate | 0.05 | 0 | 0.10 | 0 |
| Other ingredients | 7.00 | 7.00 | 7.00 | 7.00 |
| Total | 100.00 | 100.00 | 100.00 | 100.00 |
| Skin irritation | A | — | A | — |
| Skin atrophy | A | A | B | A |

With respect to the patches containing memantine hydrochloride, the results of Test 29 are shown in Table 10. With the patches of Comparative Examples 8 and 9, the skin irritation was not mitigated sufficiently.

TABLE 10

|  | Test 29 | | |
|---|---|---|---|
|  | Comp. Ex. 8 | Comp. Ex. 9 | Ref. Ex. 7 |
| Memantine hydrochloride | 16.00 | 16.00 | 16.00 |
| SIS BLOCK COPOLYMER | 13.24 | 13.24 | 13.24 |
| Polyisobutylene | 5.67 | 5.67 | 5.67 |
| Alicyclic saturated hydrocarbon resin | 32.1395 | 32.1393 | 32.14 |
| Liquid paraffin | 22.69 | 22.69 | 22.69 |
| Sodium hydroxide | 3.26 | 3.26 | 3.26 |
| Diflucortolone valerate | 0.0005 | 0.0007 | 0 |
| Other ingredients | 7.00 | 7.00 | 7.00 |
| Total | 100.00 | 100.00 | 100.00 |
| Skin irritation | B | B | — |
| Skin atrophy | A | A | A |

With respect to the patches containing amlodipine besilate, the results of Tests 21 to 24 are shown in Tables 11 and 12. With the patch of Comparative Example 6, skin atrophy was recognized.

TABLE 11

|  | Test 21 | | Test 22 | |
|---|---|---|---|---|
|  | Ex. 16 | Ref. Ex. 8 | Ex. 17 | Ref. Ex. 8 |
| Amlodipine besilate | 2.00 | 2.00 | 2.00 | 2.00 |
| SIS BLOCK COPOLYMER | 21.97 | 21.97 | 21.97 | 21.97 |
| Alicyclic saturated hydrocarbon resin | 48.319 | 48.32 | 48.315 | 48.32 |
| Liquid paraffin | 17.57 | 17.57 | 17.57 | 17.57 |
| Oleyl alcohol | 10.00 | 10.00 | 10.00 | 10.00 |
| Diflucortolone valerate | 0.001 | 0 | 0.005 | 0 |
| Other ingredients | 0.14 | 0.14 | 0.14 | 0.14 |
| Total | 100.00 | 100.00 | 100.00 | 100.00 |
| Skin irritation | A | — | A | — |
| Skin atrophy | A | A | A | A |

TABLE 12

|  | Test 23 | | Test 24 | |
|---|---|---|---|---|
|  | Ex. 18 | Ref. Ex. 8 | Comp. Ex. 6 | Ref. Ex. 8 |
| Amlodipine besilate | 2.00 | 2.00 | 2.00 | 2.00 |
| SIS BLOCK COPOLYMER | 21.95 | 21.97 | 21.94 | 21.97 |
| Alicyclic saturated hydrocarbon resin | 48.3 | 48.32 | 48.27 | 48.32 |
| Liquid paraffin | 17.56 | 17.57 | 17.55 | 17.57 |
| Oleyl alcohol | 10.00 | 10.00 | 10.00 | 10.00 |
| Diflucortolone valerate | 0.05 | 0 | 0.10 | 0 |
| Other ingredients | 0.14 | 0.14 | 0.14 | 0.14 |
| Total | 100.00 | 100.00 | 100.00 | 100.00 |
| Skin irritation | A | — | A | — |
| Skin atrophy | A | A | B | A |

With respect to the patches containing amlodipine besilate, the results of Test 30 are shown in Tables 13. With the patches of Examples 22 and 23, the skin irritation was mitigated, and skin atrophy was not recognized.

TABLE 13

|  | Test 30 | | |
|---|---|---|---|
|  | Ex. 22 | Ex. 23 | Ref. Ex. 8 |
| Amlodipine besilate | 2.00 | 2.00 | 2.00 |
| SIS BLOCK COPOLYMER | 21.97 | 21.97 | 21.97 |
| Alicyclic saturated hydrocarbon resin | 48.3195 | 48.3193 | 48.32 |
| Liquid paraffin | 17.57 | 17.57 | 17.57 |
| Oleyl alcohol | 10.00 | 10.00 | 10.00 |
| Diflucortolone valerate | 0.0005 | 0.0007 | 0 |
| Other ingredients | 0.14 | 0.14 | 0.14 |
| Total | 100.00 | 100.00 | 100.00 |
| Skin irritation | A | A | — |
| Skin atrophy | A | A | A |

With respect to the patches containing ropinirole hydrochloride, the results of Tests 25 to 28 are shown in Tables 14 and 15. With the patch of Comparative Example 7, skin atrophy was recognized.

TABLE 14

|  | Test 25 | | Test 26 | |
| --- | --- | --- | --- | --- |
|  | Ex. 19 | Ref. Ex. 9 | Ex. 20 | Ref. Ex. 9 |
| Ropinirole hydrochloride | 15.00 | 15.00 | 15.00 | 15.00 |
| SIS BLOCK COPOLYMER | 14.08 | 14.08 | 14.08 | 14.08 |
| Polyisobutylene | 6.03 | 6.03 | 6.03 | 6.03 |
| Alicyclic saturated hydrocarbon resin | 40.229 | 40.23 | 40.225 | 40.23 |
| Liquid paraffin | 8.04 | 8.04 | 8.04 | 8.04 |
| Diflucortolone valerate | 0.001 | 0 | 0.005 | 0 |
| Other ingredients | 16.62 | 16.62 | 16.62 | 16.62 |
| Total | 100.00 | 100.00 | 100.00 | 100.00 |
| Skin irritation | A | — | A | — |
| Skin atrophy | A | A | A | A |

TABLE 15

|  | Test 27 | | Test 28 | |
| --- | --- | --- | --- | --- |
|  | Ex. 21 | Ref. Ex. 9 | Comp. Ex. 7 | Ref. Ex. 9 |
| Ropinirole hydrochloride | 15.00 | 15.00 | 15.00 | 15.00 |
| SIS BLOCK COPOLYMER | 14.07 | 14.08 | 14.06 | 14.08 |
| Polyisobutylene | 6.03 | 6.03 | 6.03 | 6.03 |
| Alicyclic saturated hydrocarbon resin | 40.19 | 40.23 | 40.16 | 40.23 |
| Liquid paraffin | 8.04 | 8.04 | 8.03 | 8.04 |
| Diflucortolone valerate | 0.05 | 0 | 0.10 | 0 |
| Other ingredients | 16.62 | 16.62 | 16.62 | 16.62 |
| Total | 100.00 | 100.00 | 100.00 | 100.00 |
| Skin irritation | A | — | A | — |
| Skin atrophy | A | A | B | A |

With respect to the patches containing ropinirole hydrochloride, the results of Tests 31 and 32 are shown in Tables 16 and 17. With the patches of Comparative Examples 10 to 12, the skin irritation was not sufficiently mitigated.

TABLE 16

|  | Test 31 | | |
| --- | --- | --- | --- |
|  | Comp. Ex. 10 | Comp. Ex. 11 | Ref. Ex. 9 |
| Ropinirole hydrochloride | 15.00 | 15.00 | 15.00 |
| SIS BLOCK COPOLYMER | 14.08 | 14.08 | 14.08 |
| Polyisobutylene | 6.03 | 6.03 | 6.03 |
| Alicyclic saturated hydrocarbon resin | 40.2295 | 40.2293 | 40.23 |
| Liquid paraffin | 8.04 | 8.04 | 8.04 |
| Diflucortolone valerate | 0.0005 | 0.0007 | 0 |
| Other ingredients | 16.62 | 16.62 | 16.62 |
| Total | 100.00 | 100.00 | 100.00 |
| Skin irritation | B | B | — |
| Skin atrophy | A | A | A |

TABLE 17

|  | Test 32 | | | |
| --- | --- | --- | --- | --- |
|  | Comp. Ex. 12 | Ex. 24 | Ex. 25 | Ref. Ex. 9 |
| Ropinirole hydrochloride | 20.00 | 20.00 | 20.00 | 20.00 |
| SIS BLOCK COPOLYMER | 12.937 | 12.937 | 12.937 | 12.937 |
| Polyisobutylene | 5.544 | 5.544 | 5.544 | 5.544 |
| Alicyclic saturated hydrocarbon resin | 36.9633 | 36.914 | 36.864 | 36.964 |
| Liquid paraffin | 7.393 | 7.393 | 7.393 | 7.393 |
| Diflucortolone valerate | 0.0007 | 0.05 | 0.1 | 0 |
| Other ingredients | 17.162 | 17.162 | 17.162 | 17.162 |
| Total | 100.00 | 100.00 | 100.00 | 100.00 |
| Skin irritation | B | A | A | — |
| Skin atrophy | A | A | A | A |

The invention claimed is:

1. A patch comprising an adhesive layer on a backing, wherein:
    the adhesive layer contains an adhesive base, a skin irritant drug or a pharmaceutically acceptable salt thereof, and diflucortolone valerate,
    the skin irritant drug is selected from the group consisting of asenapine, rivastigmine, rotigotine, memantine, ropinirole, and a pharmaceutically acceptable salt thereof,
    the content of the diflucortolone valerate is 0.0009 to 0.08% by mass based on the total mass of the adhesive layer, and
    wherein when the skin irritant drug is asenapine, the adhesive layer comprises a mass ratio of asenapine or a pharmaceutically acceptable salt thereof and diflucortolone valerate of 12.5:1 to 27778:1;
    wherein when skin irritant drug is rivastigmine, the adhesive layer comprises a mass ratio of rivastigmine or a pharmaceutically acceptable salt thereof and diflucortolone valerate of 75:1 to 33333:1;
    wherein when the skin irritant drug is rotigotine, the adhesive layer comprises a mass ratio of rotigotine or a pharmaceutically acceptable salt thereof and diflucortolone valerate is 62.5:1 to 20000:1;
    wherein when the skin irritant drug is memantine, the adhesive layer comprises a mass ratio of memantine or a pharmaceutically acceptable salt thereof and diflucortolone valerate is 1.25:1 to 55556:1; and
    wherein when the skin irritant drug is ropinirole, the adhesive layer comprises a mass ratio of ropinirole or a pharmaceutically acceptable salt thereof and diflucortolone valerate is 6.25:1 to 55556:1.

2. The patch according to claim 1, wherein the adhesive base comprises at least one adhesive base selected from the group consisting of a rubber based adhesive base, an acrylic adhesive base, and a silicone based adhesive base.

* * * * *